US009005910B2

(12) United States Patent
Ohiro et al.

(10) Patent No.: US 9,005,910 B2
(45) Date of Patent: Apr. 14, 2015

(54) COMPLEX OF LABELED PROBES AND WATER-SOLUBLE CARRIER

(75) Inventors: Yoshiyuki Ohiro, Tochigi (JP); Susumu Takayasu, Tochigi (JP)

(73) Assignees: Eiken Kagaku Kabushiki Kaisha, Taito-ku (JP); Advanced Life Science Institute, Inc., Saitama (JP)

( * ) Notice: Subject to any disclaimer, the term of this patent is extended or adjusted under 35 U.S.C. 154(b) by 0 days.

(21) Appl. No.: 13/640,821

(22) PCT Filed: Apr. 13, 2011

(86) PCT No.: PCT/JP2011/059150
§ 371 (c)(1),
(2), (4) Date: Dec. 21, 2012

(87) PCT Pub. No.: WO2011/129357
PCT Pub. Date: Oct. 20, 2011

(65) Prior Publication Data
US 2013/0230897 A1  Sep. 5, 2013

(30) Foreign Application Priority Data

Apr. 14, 2010  (JP) ................................ 2010-092953

(51) Int. Cl.
*G01N 33/53* (2006.01)
*G01N 33/532* (2006.01)
*G01N 33/548* (2006.01)
*G01N 33/58* (2006.01)
*G01N 33/543* (2006.01)

(52) U.S. Cl.
CPC ........ *G01N 33/581* (2013.01); *G01N 33/54353* (2013.01); *G01N 33/532* (2013.01); *G01N 33/582* (2013.01)

(58) Field of Classification Search
None
See application file for complete search history.

(56) References Cited

U.S. PATENT DOCUMENTS

| 5,378,608 | A | 1/1995 | Marui et al. | |
|---|---|---|---|---|
| 6,252,053 | B1 | 6/2001 | Ohbayashi et al. | |
| 2001/0005583 | A1 | 6/2001 | Ohbayashi et al. | |
| 2007/0254311 | A1* | 11/2007 | Alagic et al. .................. | 435/7.5 |
| 2007/0298435 | A1 | 12/2007 | Aoyagi et al. | |
| 2008/0108097 | A1* | 5/2008 | Ohmiya et al. ................ | 435/8 |
| 2008/0153089 | A1* | 6/2008 | Aoyagi .......................... | 435/6 |
| 2009/0208932 | A1 | 8/2009 | Nice et al. | |
| 2011/0039260 | A1* | 2/2011 | Jenison et al. ................ | 435/6 |

FOREIGN PATENT DOCUMENTS

| EP | 0618192 A1 | 10/1994 |
|---|---|---|
| JP | 11295313 A | 10/1999 |
| JP | 2003194821 A | 7/2003 |
| JP | 2008122302 A | 5/2008 |
| JP | 2009244101 A | 10/2009 |
| WO | 0173123 A2 | 10/2001 |
| WO | 2008152424 A2 | 12/2008 |

OTHER PUBLICATIONS

Yu et al., Investigative Ophthalmology & Visual Science 49(2): 522-527, Feb. 2008.*
Grodzki et al, Immunocytochemical Methods and Protocols, in methods in Molcular Biology 588: 33-41, 2010.*
International Preliminary Report on Patentability from corresponding PCT/JP2011/059150, Dated Nov. 6, 2012.
Extended European Search Report for Application No. 11768878.8 dated Oct. 21, 2013.
Fukuda et al., "Bioluminescent Enzyme Immunoassay with Biotinylated Firefly Luciferase", Journal of Clinical Ligand Assay, 1998, pp. 358-362, vol. 21, No. 4.
Sakamaki et al., "Bioluminescent Enzyme Immunoassay for the Detection of the Norovirus Capsid Antigen", Clinical and Vaccine Immunology, 2012, pp. 1949-1954, vol. 19, No. 12.
Seto et al., "Development of Highly Sensitive Bioluminescent Enzyme Immunoassay with Ultra-Wide Measurable Range for Thyroid-Stimulating Hormone Using Firefly Luciferase", Analytica Chimica Acta, 2001, pp. 19-26, vol. 429.
Seto et al., "Development of Ultra-High Sensitivity Bioluminescent Enzyme Immunoassay for Prostate-Specific Antigen (PSA) Using Firefly Luciferase", Luminescence, 2001, pp. 285-290, vol. 16.
Office Action for CN Application 201180018682.3 dated Mar. 28, 2014.
Office Action English Translation for CN Application 201180018682.3 dated Mar. 28, 2014.

* cited by examiner

*Primary Examiner* — Phuong Huynh
(74) *Attorney, Agent, or Firm* — Thompson Coburn LLP

(57) ABSTRACT

The purpose is to produce, with high reproducibility, a complex of labeled probes and a carrier, said complex being to be used for detecting and measuring a target substance to be measured with high sensitivity and high stability. The means for accomplishing the purpose is that a label is bound to a probe-water soluble carrier conjugate using specific binding of an avidin compound such as avidin, streptavidin, etc. to biotin, and the binding of the avidin compound to the probe is performed before the binding to the carrier. Namely, after conjugating the avidin compound to a substance which is capable of binding to the target substance, the conjugate is bound to a high-molecule water-soluble carrier to produce a complex of the avidinized probes and the water-soluble carrier. Then the complex of the avidinized probes and the water-soluble carrier is mixed with a biotinylated label. Thus, a stable complex of the labeled probes and the water-soluble carrier, which enables the highly sensitive detection and measurement of the target substance, can be obtained with high reproducibility via the specific binding of the avidin compound to biotin.

19 Claims, 3 Drawing Sheets

COMPLEX OF LABELED PROBES AND WATER-SOLUBLE CARRIER

TECHNICAL FIELD

The present invention relates to a method for producing the complex of labeled probes and a water-soluble carrier, in which a plurality of probes and further labels are bound to a water-soluble carrier, the complex of labeled probes and a water-soluble carrier produced by said method, and a method of using the same. The use of this complex of labeled probes and a water-soluble carrier allows detection and measurement to be performed with high sensitivity and stability.

BACKGROUND ART

In a method for detecting and measuring a target substance using a probe-label conjugate, wherein the probe specifically binds to the target substance and further the amount of the labels bound to the target substance via the probe is referred to as an indicator, the sensitivity is generally determined by the number of molecules of the probe and label. That is to say, since the number of molecules of the label which binds to one molecular of the probe is limited, the ratio thereof determines the sensitivity.

Thus, higher sensitivity with an improved reactivity has been achieved in such a manner that the probe itself is polymerized to produce a polymer thereby increasing the molecular weight thereof, and thus increasing the number of molecules of the label which binds to the polymer (Patent Literature 1). However, since it is not easy to control the polymerization of the probes, it has not been put to practical use.

Further, a label-probe complex having a high molecular weight and a large number of the labels, which is produced by covalently bonding one or more enzymatic labels and probes separately to a carrier such as polylysine and aminodextran, has been proposed (Patent Literature 2). However, although this technique increases reactivity, it also increases a reaction at a blank value, and thus does not provide higher sensitivity in detecting and measuring.

In addition, the following have been proposed: a label-probe complex in which one or more enzymatic labels are bound to a carrier such as polylysine and one or more probes are bound to the carrier through the labels on the carrier (Patent Literature 3); a water-soluble carrier-probe complex in which one or more probes are bound to a carrier such as dextran and one or more labels are bound to the carrier through the probes on the carrier (Patent Literature 4); a probe complex in which a hydrophilic intermediate is bound to a carrier and one or more probes and detection markers are bound to the intermediate (Patent Literature 5); and a blocked label-probe in which two or more carriers are bound to an enzymatic label to produce a complex and one or more probes are bound to the complex (Patent Literature 6).

However, the above-mentioned prior art involves a technical problem that a reaction at a blank value also increases while reactivity increases, and it has been difficult to obtain a highly sensitive and stable complex in the case of evaluating the reactivity as a signal-to-noise ratio. Further, when a carrier is first bound to the probe or label in the formation of a complex, it has been difficult to produce a desired complex with favorable reproducibility, resulting from multifunctionality of the carrier.

CITATION LIST

Patent Literatures

Patent Literature 1: Japanese Patent Application Laid-Open (JP-A) No. 11-295313
Patent Literature 2: JP-A No. 2000-088850
Patent Literature 3: JP-A No. 2001-181299
Patent Literature 4: JP-A No. 2003-194821
Patent Literature 5: WO 2006/011543
Patent Literature 6: WO 2006/070732

SUMMARY OF INVENTION

Technical Problem

In order to detect and measure a target substance using a probe-label conjugate, wherein the probe specifically binds to the target substance and further the amount of the labels bound to the target substance via the probe is referred to as an indicator, a large amount of the labels needs to be included in one molecular of the probe-label conjugate. Thus, it is necessary to produce a probe-label conjugate having a large molecular weight.

However, in the case of using a carrier for forming the conjugate having a large molecular weight, the reactivity indeed increases but at the same time a reaction at a blank value also increases; consequently, it is difficult to obtain the high-sensitive and stable complex. Further, when the binding of a carrier and probes or labels is performed as the first step of the formation of a complex, it is difficult to produce a desired complex with favorable reproducibility, resulting from multifunctionality of the carrier. Then, a conjugate that solves the above-mentioned problem and a method for stably producing the conjugate are expected.

Solution to Problem

The inventors have thought of utilizing a specific binding between an avidin compound and biotin in binding a probe to a label in the production of the complex of labeled probes and a carrier, and have found out that the performance of the binding of an avidin compound and the probe before the binding of them to the carrier allows an extremely highly sensitive and stable complex to be produced with favorable reproducibility. In addition, the inventors have found out that, in performing a chemical modification of the probe for the chemical bonding, the introduction of one or more thiol groups into the probe has no influence on the binding capacity of the probe. Furthermore, the inventors have used, as a carrier, a water-soluble carrier to construct the complex of labeled probes and a water-soluble carrier useful for detection and measurement with high sensitivity and stability.

That is to say, the present invention relates to a method for producing the complex of labeled probes and a water-soluble carrier, which includes the following steps.

Step 1. binding a probe having one or more thiol groups, being capable of binding to a target substance, to an avidin compound having one or more maleimide groups to obtain a probe conjugate;
Step 2. next, binding the probe conjugate having one or more thiol groups to a high-molecular water-soluble carrier having one or more maleimide groups to obtain a complex of the probe conjugate and the water-soluble carrier; and
Step 3. further, mixing the complex of the probe conjugate and the water-soluble carrier with a biotinylated label to bind the avidin compound in the complex of the probe conjugate and the water-soluble carrier to biotin in the biotinylated label.

The present invention also relates to the complex of labeled probes and a water-soluble carrier produced by the above-mentioned steps.

The present invention further relates to a method for measurement, immunoassay or high-sensitive measurement using the complex of labeled probes and a water-soluble carrier produced by the above-mentioned steps.

In the present invention, the 'probe' means a binding partner that interacts with a target substance, and examples thereof may include, but not limited to, an antibody or an antibody fragment, protein G, protein A, protein L, lectin, or a receptor. Further, examples of the antibody or the antibody fragment may include, but not limited to, Fab', $F(ab')_2$, Fab, or IgG.

Further, two or more kinds of antibodies or antibody fragments may be used as the antibody or the antibody fragment.

In the present invention, the 'avidin compound' means a compound that forms a stable complex with a biotin compound, such as avidin, which is a low-molecular basic glycoprotein, and a protein similar thereto or fragments thereof; examples of the 'avidin compound' may include, but not limited to, avidin or streptavidin.

In the present invention, the 'water-soluble carrier' preferably has a molecular weight of 500,000 or more. Examples of the water-soluble carrier of the present invention may include, but not limited to, dextran, aminodextran, dextrin, cluster dextrin, ficoll, or pullulan.

The present invention uses 'biotinylated label'. Here, the 'biotin' is one of vitamin B complexes and is known to bind to avidin very strongly. Examples of the 'biotinylated label' in the present invention may include, but not limited to, biotinylated luciferase, biotinylated alkaline phosphatase, biotinylated POD (peroxidase), biotinylated GOD (glucose oxidase), biotinylated FITC (fluorescein isothiocyanate), biotinylated acridinium, biotinylated acridinium derivative, or biotinylated tris(2,2' bipyridyl)ruthenium(II). Any known means including chemical modification may be utilized for binding the biotin and label in the 'biotinylated label', and genetic recombination is utilized particularly preferably, because no chemical modification is required for the chemical bonding and thus the activity of the label is not deteriorated.

In Step 1 according to the present invention, first, in the case where a probe being capable of binding to a target substance does not have sufficient thiol groups, one or more thiol groups are introduced into the probe. Any known methods may be used for the introduction of thiol groups; in the case where the probe is an antibody or an antibody fragment, the introduction of thiol groups by using a reducing agent such as 2-mercaptoethanol to reduce one or more inherent disulfide bonds is particularly advantageous because the influence on the binding capacity of the probe may be minimized.

Next, one or more maleimide groups are introduced into an avidin compound. Any known methods may be used for the introduction of maleimide groups; for example, a known maleimide reagent such as Sulfo-KMUS (DOJINDO LABORATORIES) may be used therefor.

Any known methods may be used for binding the probe having thiol groups, which may bind to a target substance, to the avidin compound having maleimide groups. For example, each of the probe and avidin compound is dissolved in a buffer solution at an appropriate concentration and then the both solutions are reacted to perform a binding reaction.

Further, in order to avoid a nonspecific reaction in the subsequent steps, unreacted maleimide groups may be blocked by using a thiol reagent such as 2-mercaptoethanol after completing the above-mentioned binding reaction. A probe-avidin compound conjugate after being blocked may be purified by any known methods such as gel filtration.

In Step 2 according to the present invention, first, one or more thiol groups are introduced into the probe-avidin compound conjugate produced in Step 1. Any known methods, such as to use 2-iminothiolane, may be used for the introduction of thiol groups.

Any known methods may be used for the introduction of one or more maleimide groups into a water-soluble carrier. For example, a water-soluble carrier is reacted with an acid to introduce one or more carboxyl groups, and after removing the acid by dialysis or the like, the carboxyl groups are replaced with amino groups using a known amino group-introducing reagent such as ethylenediamine. After being replaced, unreacted amino group-introducing reagent is removed by dialysis or the like, and the water-soluble carrier having maleimide groups may be obtained by adding and reacting a known maleimide reagent.

Any known methods may be used for binding the probe-avidin compound conjugate having one or more thiol groups to the water-soluble carrier having one or more maleimide groups. Further, in order to avoid a nonspecific reaction in the subsequent steps, unreacted maleimide groups introduced into the water-soluble carrier are preferably blocked by using a thiol reagent such as 2-mercaptoethanol after completing the binding reaction. A complex of the probe conjugate and the water-soluble carrier after being blocked may be purified by any known methods such as gel filtration.

In Step 3 according to the present invention, the above-mentioned complex of the probe conjugate and the water-soluble carrier is mixed with a biotinylated label to bind the avidin compound in the complex of the probe conjugate and the water-soluble carrier to biotin in the biotinylated label. As described above, affinity between the avidin compound and biotin is so strong that the binding reaction of the avidin compound and biotin may be performed in such a manner that each the complex of the probe conjugate and the water-soluble carrier and the biotinylated label is prepared at an appropriate concentration and then the both prepared solutions are mixed.

The complex of labeled probes and a water-soluble carrier produced by the steps according to the present invention may be used in any known methods for measurement because the complex is reacted with a target substance, which is a target of the probe, with high sensitivity and stability. Further, in the case where the probe is an antibody or an antibody fragment, the complex of labeled probes and a water-soluble carrier according to the present invention may be used in any known methods for immunoassays.

In addition, the complex of labeled probes and a water-soluble carrier produced by the steps according to the present invention is extremely stable even after long-term preservation. The stability with time was retained even under an accelerated stability test at 37° C. for one week.

The present invention is illustrated below by using biotinylated luciferase for the biotinylated label, Fab' for the probe, streptavidin for the avidin compound, and dextran (T2000) for the water-soluble carrier as an example, but is not limited to the example.

$F(ab')_2$ obtained by the digestion of an IgG antibody with pepsin is subjected to a reduction treatment by adding 2-mercaptoethanol thereto and thereafter purified by gel filtration to obtain Fab' having thiol groups.

On the other hand, streptavidin is treated by adding a maleimide-introducing reagent and thereafter purified by gel filtration to obtain streptavidin introduced with one or more maleimide groups.

Fab' introduced with one or more thiol groups and streptavidin introduced with one or more maleimide groups thus obtained are mixed and reacted, and then adding thereto 2-mercaptoethanol to block unreacted maleimide groups, followed by purifying by gel filtration to obtain a Fab'-streptavidin conjugate.

The Fab'-streptavidin conjugate thus obtained is reacted by adding 2-iminothiolane and thereafter purified by gel filtration to obtain a Fab'-streptavidin conjugate introduced with one or more thiol groups.

One or more amino groups are introduced into dextran (T2000) to produce aminodextran, and then the aminodextran is reacted by adding a maleimide reagent, followed by purified by gel filtration to obtain dextran (T2000) introduced with one or more maleimide groups.

The Fab'-streptavidin conjugate introduced with one or more thiol groups and the dextran (T2000) introduced with one or more maleimide groups thus obtained are mixed and reacted, and then adding thereto 2-mercaptoethanol to block unreacted maleimide groups, followed by purifying by gel filtration to obtain a complex of the Fab'-streptavidin conjugate and dextran.

The complex of the Fab'-streptavidin conjugate and dextran (T2000) thus obtained is mixed and reacted with biotinylated luciferase to obtain a complex of luciferase-labeled Fab' and dextran (T2000).

A method for high-sensitive detection and measurement is completed in such a manner that the obtained complex of luciferase-labeled Fab' and dextran (T2000) is used as a labeled antibody and combined with a solid phase, onto which another antibody prepared separately has been immobilized, to perform sandwich immunoassays.

Although the inventors do not intend to be bound by a theory, it is considered that the production of the extremely high-sensitive and stable complex of labeled probes and a water-soluble carrier with favorable reproducibility by the present invention as compared with the prior art results mainly from that the probe and label are bound utilizing a high affinity between the avidin compound and biotin and that the probe and avidin compound are bound before bound to the carrier. With regard to the binding of probe and avidin compound and the binding of avidin compound and biotin, the ratio of molecular numbers or the like with regard to the binding can be controlled easily; accordingly, the complex of labeled probes and a water-soluble carrier having the same structure will be produced stably with favorable reproducibility. Further, it is considered that the complex of labeled probes and a water-soluble carrier thus produced stably has a structure extremely appropriate for increasing only a specific reaction composing a signal while relatively restricting a nonspecific reaction composing a noise.

Advantageous Effects of Invention

By performing the present invention, a high-sensitive and stable complex of labeled probes and a water-soluble carrier, which specifically binds to a target substance, can be obtained with favorable reproducibility, and by using the complex of labeled probes and a water-soluble carrier, a high-sensitive and stable detection and measurement can be accomplished.

DESCRIPTION OF EMBODIMENTS

Figure 1:
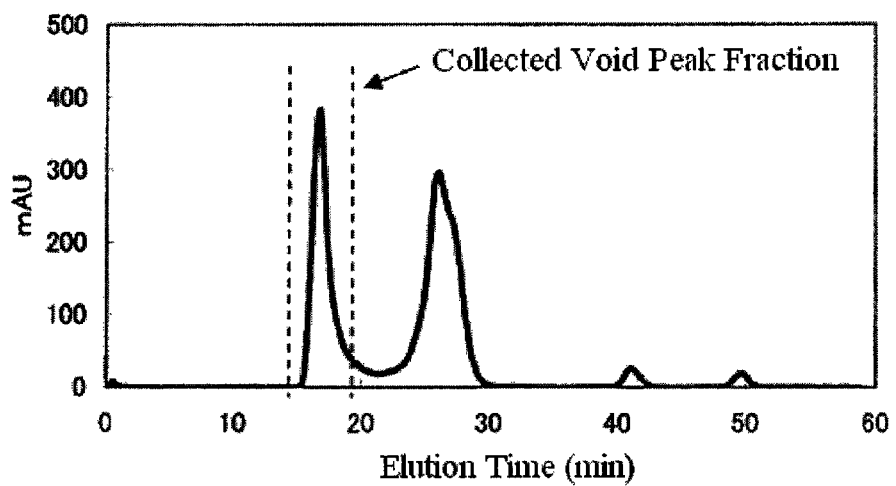
FIG. 1 is an elution pattern of a complex of IgG-streptavidin conjugate and dextran (T2000).
Figure 2:
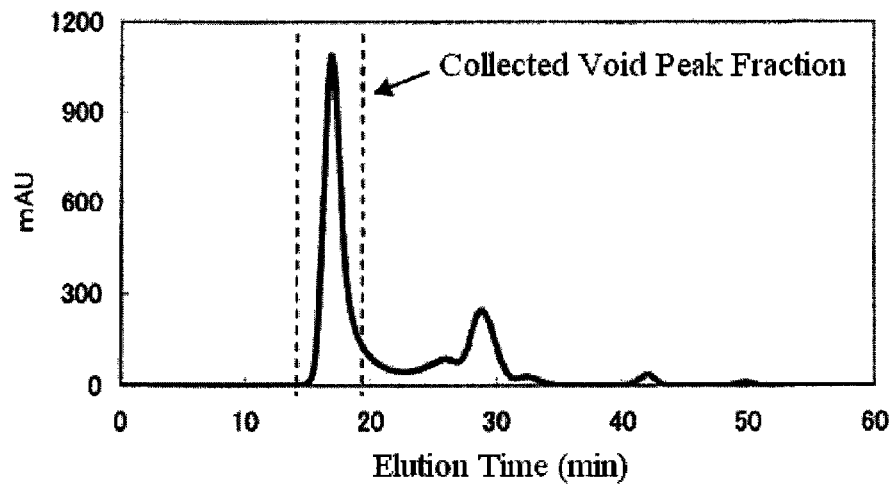
FIG. 2 is an elution pattern of a complex of Fab' (c11-9+c11-14)-streptavidin conjugate and dextran (T2000).
Figure 3:
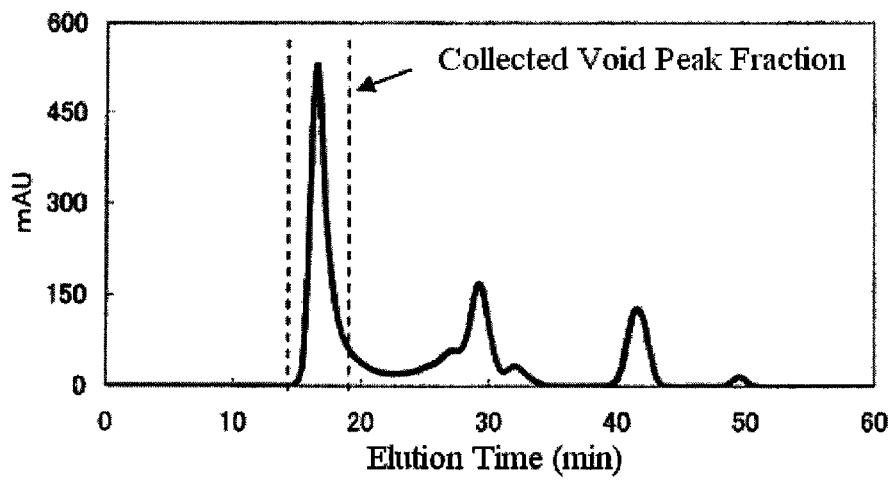
FIG. 3 is an elution pattern of a complex of Fab' (c11-9)-streptavidin conjugate and dextran (T2000).
Figure 4:
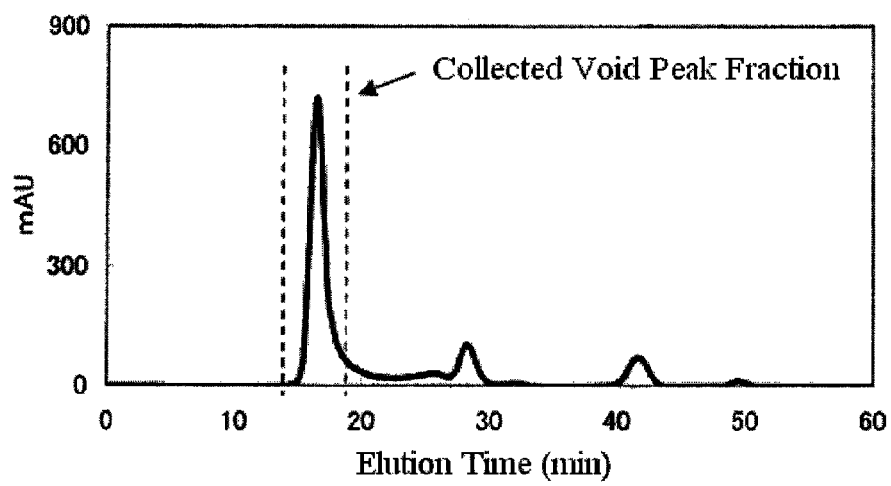
FIG. 4 is an elution pattern of a complex of Fab' (c11-14)-streptavidin conjugate and dextran (T2000).
Figure 5:
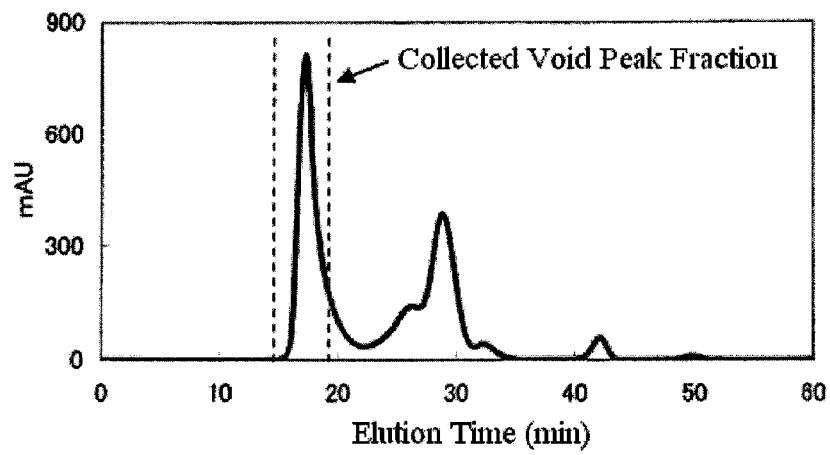
FIG. 5 is an elution pattern of a complex of Fab' (c11-9+c11-14)-streptavidin conjugate and dextran (T500).

A target substance in a sample is detected and measured as follows: an insoluble carrier onto which one or more probes, which specifically bind to a target substance, are immobilized is reacted with a sample followed by washing to remove the sample, and thereafter the complex of labeled probes and a water-soluble carrier is added thereto, reacted and washed again, and then finally measuring the activity of a label on the insoluble carrier.

EXAMPLE 1

Preparation of IgGs Having One or More Thiol Groups by Reduction Treatment

Anti-HCV core antigen mouse monoclonal IgG antibodies c11-9 and c11-14 were dissolved in 0.1M phosphate buffer (pH 7.2) to prepare 5 mg/mL solution of each. 30 µL of 0.2 M 2-mercaptoethanol (Wako Pure Chemical Industries, Ltd.) was added to 300 µL of each IgG solution, and reacted at 37° C. for 1.5 hours. After being reacted, each solution was purified by gel filtration with PD-10 (GE Healthcare) to obtain IgG having thiol groups obtained by reducing one or more disulfide bonds present inherently in the antibody. As a result of quantification of the number of thiol groups in each solution, the presence of 8.0 thiol groups per one molecule of IgG was confirmed.

EXAMPLE 2

Preparation of Fab's Having One or More Thiol Groups by Reduction Treatment

Anti-HCV core antigen mouse monoclonal IgG antibodies c11-9 and c11-14 were prepared with 0.1 M sodium acetate buffer (pH 4.5) so as to become 10 mg/mL. Next, 0.2 mg of pepsin was added to 1 mL of these IgG solutions and stirred at 37° C. for 6 hours to complete the pepsin digestion of IgGs. After the pepsin digestion, the solutions were neutralized with 2N NaOH and purified with Superdex 200 column (GE Healthcare) to obtain F(ab')$_2$.

130 µL of 0.2 M 2-mercaptoethanol (Wako Pure Chemical Industries, Ltd.) was added to each 1300 µL of 3.0 mg/mL F(ab')$_2$ and then reacted at 37° C. for 1.5 hours. After being reacted, the solutions were purified by gel filtration with PD-10 (GE Healthcare) to obtain Fab' having thiol groups obtained by reducing one or more disulfide bonds present inherently in the antibody. As a result of quantification of the number of thiol groups in each solution, the presence of 3.3 thiol groups per one molecular of c11-9 Fab' and 3.4 thiol groups per one molecular of c11-14 Fab' was confirmed.

EXAMPLE 3

Introduction of One or More Maleimide Groups into Streptavidin 20 mg of streptavidin (MP Bio) dissolved in 2 mL of 0.1 M phosphate buffer (pH 7.2) was mixed with 133 μL of a maleimide reagent Sulfo-KMUS (DOJINDO LABORATORIES) which has been dissolved in dimethylformamide so as to become 6 mg/mL. After reacting at 30° C. for 1 hour, the solution was purified by gel filtration with PD-10 (GE Healthcare) to obtain streptavidin introduced with one or more maleimide groups. As a result of quantification of the number of maleimide groups, the presence of 3.7 maleimide groups per one streptavidin molecule was confirmed.

EXAMPLE 4

Production of IgG-Streptavidin Conjugates

Each of the IgGs of c11-9 and c11-14 introduced with one or more thiol groups produced in Example 1 was dissolved in 0.1 M phosphate buffer (pH 7.2) to prepare each 2.5 mg/mL IgG solution introduced with one or more thiol groups. On the other hand, the streptavidin introduced with one or more maleimide groups, which was produced in Example 3, was dissolved in 0.1 M phosphate buffer (pH 7.2) to prepare a 13.0 mg/mL streptavidin solution introduced with one or more maleimide groups.

Next, 38 μL of the streptavidin solution introduced with one or more maleimide groups was added to each 500 μL of the IgG solutions introduced with one or more thiol groups, and they were reacted at 30° C. for 1 hour. After being reacted, 54 μL of 0.2 M 2-mercaptoethanol (Wako Pure Chemical Industries, Ltd.) was added thereto and reacted at 4° C. overnight to block unreacted maleimide groups. After being reacted, the solutions were purified by gel filtration with Superdex 200 column (GE Healthcare) to obtain IgG-streptavidin conjugates.

EXAMPLE 5

Production of Luciferase-Labeled IgGs 8.2 μL of 61 μM biotinylated luciferase (Kikkoman Corp.) was added to 50 μL of the 10 μM IgG-streptavidin conjugates (c11-9 and c11-14) produced in Example 4, and reacted at 25° C. for 1 hour to produce luciferase-labeled IgGs.

EXAMPLE 6

Production of Fab'-Streptavidin Conjugates

Each of the Fab's of c11-9 and c11-14 introduced with one or more thiol groups produced in Example 2 was dissolved in 0.1 M phosphate buffer (pH 7.2) to prepare each 2.6 mg/mL Fab'solution introduced with one or more thiol groups. On the other hand, the streptavidin introduced with one or more maleimide groups, which was produced in Example 3, was dissolved in 0.1 M phosphate buffer (pH 7.2) to prepare a 13.0 mg/mL streptavidin solution introduced with one or more maleimide groups.

Next, 365 μl of the streptavidin solution introduced with one or more maleimide groups was added to each 1400 μL of the Fab'solutions introduced with one or more thiol groups, and they were reacted at 30° C. for 1 hour. After being reacted, 177 μL of 0.2 M 2-mercaptoethanol (Wako Pure Chemical Industries, Ltd.) was added thereto and reacted at 4° C. overnight to block unreacted maleimide groups. After being reacted, the solutions were purified by gel filtration with Superdex 200 column (GE Healthcare) to obtain Fab'-streptavidin conjugates.

EXAMPLE 7

Production of Luciferase-Labeled Fab's 4.3 μL of 61 μM biotinylated luciferase (Kikkoman Corp.) was added to 10 of the 26.4 μM the Fab'-streptavidin conjugates (c11-9 or c11-14) produced in Example 6, and reacted at 25° C. for 1 hour to produce luciferase-labeled Fab's.

EXAMPLE 8

Introduction of One or More Maleimide Groups into One or More Amino Groups-Introduced Dextran Each 2 g of dextran (T2000) and dextran (T500) and 4.7 g of monochloroacetic acid were dissolved in a 50 mL solution of 3 N NaOH, and stirred at room temperature for 70 minutes to introduce one or more carboxyl groups into dextran (T2000) and dextran (T500). Next, 0.2 g of sodium dihydrogen phosphate was added thereto, and then neutralizing the mixed solutions with 6 N HCl to stop the reaction, followed by dialysis to remove unreacted monochloroacetic acid.

After the dialysis, 16.4 g of ethylenediamine and 1.2 g of 1-ethyl-3-(3-dimethylaminopropyl)carbodiimide were added thereto and stirred at room temperature for 4 hours thereby converting the carboxyl groups, which had been introduced into dextran (T2000) and dextran (T500), into amino groups. Next, unreacted ethylenediamine and carbodiimide were removed by dialysis, followed by freeze-drying to recover aminodextran (T2000) and aminodextran (T500).

Each 1.5 mg of aminodextran (T2000) and aminodextran (T500) was dissolved in 3 mL of 0.1 M phosphate buffer (pH 7.2), and 30 μL of a maleimide reagent Sulfo-KMUS (DOJINDO LABORATORIES) dissolved in dimethylformamide so as to become 12 mg/mL was added thereto and reacted at 37° C. for 30 minutes. After being reacted, the solutions were purified by gel filtration with PD-10 (GE Healthcare) to obtain aminodextran (T2000) and aminodextran (T500) introduced with one or more maleimide groups. As a result of quantification of the number of maleimide groups, the presence of 294 maleimide groups per one dextran (T2000) molecule and 65 maleimide groups per one dextran (T500) molecule was confirmed.

EXAMPLE 9

Production of a Complex of IgG-Streptavidin Conjugate and Dextran

Each of the IgG-streptavidin conjugates (c11-9 or c11-14) produced in Example 4 was dissolved in 0.1 M phosphate buffer (pH 7.2) to obtain each 2.5 mg/mL solution, and then the both were mixed equally in quantity to prepare an IgG-streptavidin conjugate solution.

264 μL of the IgG-streptavidin conjugate solution was mixed with 2 μL of 2-iminothiolane (PIERCE) dissolved in dimethylformamide so as to become 1 mg/mL and then reacted at 30° C. for 30 minutes. After being reacted, the solution was purified by gel filtration with PD-10 (GE Healthcare) to obtain an IgG-streptavidin conjugate introduced with one or more thiol groups. As a result of quantification of the number of thiol groups, the presence of 4.8 thiol groups per one molecule of the IgG-streptavidin conjugate was confirmed.

Next, 290 µL of the 8.6 µM IgG-streptavidin conjugate introduced with one or more thiol groups was mixed with 40 µL of the 0.625 µM aminodextran (T2000) solution introduced with one or more maleimide groups, which was produced in Example 8, and then reacted at 30° C. for 1 hour. Thereafter, 33 µL of 0.2 M 2-mercaptoethanol (Wako Pure Chemical Industries, Ltd.) was added thereto and reacted at 4° C. overnight to block unreacted maleimide groups. After being reacted, the solution was purified by gel filtration with Superdex 200 column (GE Healthcare) to obtain a complex of the IgG-streptavidin conjugate and dextran (T2000) from a void peak fraction shown in FIG. 1.

EXAMPLE 10

Introduction of Biotinylated Luciferase into a Complex of IgG-Streptavidin Conjugate and Dextran The complex of the IgG-streptavidin conjugate and dextran (T2000) produced in Example 9 was prepared using 0.1 M phosphate buffer (pH 7.2) so that the concentration of the IgG-streptavidin conjugate became 570 nM. 300 µL of said complex solution of the IgG-streptavidin conjugate and dextran (T2000) was mixed with 3.0 µL solution of 61 µM biotinylated luciferase (Kikkoman Corp.), and then reacted at 25° C. for 1 hour to obtain a complex of luciferase-labeled IgG and dextran (T2000).

EXAMPLE 11

Production of Complexes of Fab'-Streptavidin Conjugate and Dextran

420 µL of the ell-9 Fab'-streptavidin conjugate with 4.0 mg/mL and 646 µL of the c11-14 Fab'-streptavidin conjugate with 2.6 mg/mL, which were produced in Example 6, was mixed with 2 µL of 2-iminothiolane (PIERCE) dissolved in dimethylformamide so as to become 1 mg/mL, and then reacted at 30° C. for 30 minutes.

After being reacted, the solutions were purified by gel filtration with PD-10 (GE Healthcare) to obtain each Fab'-streptavidin conjugate introduced with one or more thiol groups. As a result of quantification of the number of thiol groups, the presence of 4.6 thiol groups per one molecule of the c11-9 Fab'-streptavidin conjugate, while 3.0 thiol groups per one molecule of the c11-14 Fab'-streptavidin conjugate was confirmed.

Next, the aminodextrans (T2000) and (T500) introduced with one or more maleimide groups, which were produced in Example 8, were mixed with the Fab'-streptavidin conjugates introduced with one or more thiol groups, and then reacted at 30° C. for 1 hour. Each aminodextran introduced with one or more maleimide groups was combined with each Fab'-streptavidin conjugate introduced with one or more thiol groups in accordance with the following concentrations and liquid volumes to produce four kinds of polymers.

1) A Complex of c11-9 and c11-14 Mixed Fab'-Streptavidin Conjugate and Dextran (T2000)

200 µl of the 21 µM c11-9 Fab'-streptavidin conjugate introduced with one or more thiol groups, 240 µL of the 18 µM c11-14 Fab'-streptavidin conjugate introduced with one or more thiol groups, and 142 µL of the 0.625 µM aminodextran (T2000) introduced with one or more maleimide groups were mixed.

2) A Complex of c11-9 Fab'-Streptavidin Conjugate and Dextran (T2000)

200 µL of the 21 µM c11-9 Fab'-streptavidin conjugate introduced with one or more thiol groups, and 71 µL of the 0.625 µM aminodextran (T2000) introduced with one or more maleimide groups were mixed.

3) A Complex of c11-14 Fab'-Streptavidin Conjugate and Dextran (T2000)

240 µL of the 18 µM c11-14 Fab'-streptavidin conjugate introduced with one or more thiol groups, and 71 µL of the 0.625 µM aminodextran (T2000) introduced with one or more maleimide groups were mixed.

4) A Complex of c11-9 and c11-14 Mixed Fab'-Streptavidin Conjugate and Dextran (T500)

200 µL of the 21 µM c11-9 Fab'-streptavidin conjugate introduced with one or more thiol groups, 240 µL of the 18 µM c11-14 Fab'-streptavidin conjugate introduced with one or more thiol groups, and 116 µl of the 2.5 µM aminodextran (T500) introduced with one or more maleimide groups were mixed.

After being reacted, 0.2 M 2-mercaptoethanol (Wako Pure Chemical Industries, Ltd.) was added by ¹⁄₁₀ of the amount of each complex solution and reacted at 4° C. overnight to block unreacted maleimide groups. The next day, the solutions were purified by gel filtration with Superdex 200 column (GE Healthcare) to obtain each complex of the Fab'-streptavidin conjugate and dextran from a void peak fraction of each sample shown in FIGS. 2 to 5.

EXAMPLE 12

Introduction of Biotinylated Luciferase into a Complex of Fab'-Streptavidin Conjugate and Dextran The four kinds of the complexes of Fab'-streptavidin conjugate and dextran produced in Example 11 were prepared with 0.1 M phosphate buffer (pH 7.2) so that the concentration of the Fab'-streptavidin conjugate became 1.8 µM. Each 100 µL of the complex solutions of Fab'-streptavidin conjugate and dextran was mixed with 3.0 µL of 61 µM biotinylated luciferase (Kikkoman Corp.), and then reacted at 25° C. for 1 hour to produce the following four complexes of luciferase-labeled Fab' and dextran.

1) A complex of luciferase-labeled c11-9–c11-14 Fab' and dextran (T2000)
2) A complex of luciferase-labeled c11-9 Fab' and dextran (T2000)
3) A complex of luciferase-labeled c11-14 Fab' and dextran (T2000)
4) A complex of luciferase-labeled c1'-9–c11-14 Fab' and dextran (T500)

EXAMPLE 13

Enzyme Immunoassay Using a Luciferase-Labeled Antibody

Anti-HCV core antigen mouse monoclonal antibodies c11-3, c11-7, and AOT3 were immobilized onto magnetic particles by a carbodiimide method using WSC to produce 0.2% antibody-immobilized magnetic particles. On the other hand, each 100 µL of normal human serum and two HCV positive sera confirmed by PCR was mixed with 100 µL of a sample treatment solution (6 M guanidine hydrochloride, 0.5 N HCl, 12.5% TritonX100 and 0.75% Tween20) and then reacted at 37° C. for 15 minutes to complete the pretreatment of the sample. After the pretreatment, 140 µL of a reaction solution (0.1 M sodium phosphate, 0.15 M NaCl, 1% BSA, 0.5% casein and 0.05% Tween20, pH 7.3) and 204 of 1 M tris buffer were mixed, and then the total 160 µL of this mixed solution was mixed with 80 µL of the pretreated sample thereby neutralizing the sample.

Next, 20 µL of the 0.2% antibody-immobilized magnetic particles were added to 240 µL of the neutralized pretreated sample, and reacted at 37° C. for 15 minutes to complete a primary reaction. After being reacted, the magnetic particles were washed with a washing solution three times and then thereto were mixed with the luciferase-labeled IgGs produced in Example 5 and the complex of luciferase-labeled IgG and dextran (T2000) produced in Example 10. Each 120 µL of the labeled antibodies which had been diluted so as to set the luciferase concentration to be 18 nM was added, stirred and thereafter reacted at 37° C. for 15 minutes. After being reacted, the magnetic particles were washed with a washing solution three times and resuspended in 100 µL of 50 mM tris buffer (pH 8.5).

100 µL of a substrate solution (luciferin) was added to a tube in which the magnetic particles had been resuspended, followed by measuring the luminescence of luciferase using Lumat LB9507 (Berthold). The luminescence measurement was conducted in such a way that luminescence was integrated for 5 seconds from 0.5 second after adding luciferin. As a result, as shown in Table 1, the complex of luciferase-labeled IgG and dextran (T2000) showed a higher luminescence value than the luciferase-labeled IgGs. When estimated from the S/N ratio of the panel sample M, it was confirmed that the reactivity was improved by approximately 50 to 100 times.

TABLE 1

| Labeled antibody | Normal human serum | Positive serum L | Positive Serum M | L/Normal | M/Normal |
|---|---|---|---|---|---|
| c11-9 IgG antibody | 218 | 216 | 314 | 1.0 | 1.4 |
| c11-14 IgG antibody | 901 | 869 | 3453 | 1.0 | 3.8 |
| c11-9 + c11-14 IgG-T2000 | 1611 | 10817 | 252624 | 6.7 | 156.8 |

(Luminescence value) (Luminescence ratio)

EXAMPLE 14

Enzyme Immunoassay by Using a Luciferase-Labeled Antibody Fragment

Enzyme immunoassay was performed in the same manner as in Example 13 except for using the products in Examples 7 and 12 as the labeled antibodies. As a result, as shown in Table 2, the complex of luciferase-labeled Fab' and dextran (T2000) or the complex of luciferase-labeled Fab' and dextran (T500) showed a higher luminescence value than the luciferase-labeled Fab's, and it was confirmed that the polymerization improved the reactivity by approximately 50 to 100 times in a similar way to the case of IgG. Further, although the improvement of the reactivity was observed in the case of individually polymerizing C11-9 or C11-14 antibody fragment, it was confirmed that more improved reactivity was observed by combining the both.

TABLE 2

| Labeled antibody | Normal human serum | Positive serum L | Positive serum M | L/Normal | M/Normal |
|---|---|---|---|---|---|
| c11-9 Fab'antibody | 144 | 140 | 208 | 1.0 | 1.4 |
| c11-14 Fab'antibody | 160 | 181 | 1407 | 1.1 | 8.8 |
| c11-9 Fab'-T2000 | 235 | 483 | 2232 | 2.1 | 9.5 |
| c11-14 Fab'-T2000 | 287 | 414 | 14642 | 1.4 | 51.0 |
| c11-9 + c11-14 Fab'-T2000 | 284 | 2435 | 211410 | 8.6 | 744.4 |
| c11-9 + c11-14 Fab'-T500 | 206 | 1436 | 115355 | 7.0 | 560.0 |

(Luminescence value) (Luminescence ratio)

EXAMPLE 15

Performance Comparison with a Polymerized Labeled Antibody Produced by Applying a Previous Method for Producing a Probe Complex Production of a Polymerized Labeled Antibody by Applying a Previous Method for Producing a Probe Complex A probe complex was produced by applying the method described in WO 2006/011543. First, 44 mg of dextran (T2000) was weighed and dissolved in 0.8 mL of 0.1 M phosphate buffer (pH 7.0), and mixed with 0.4 mL of a sodium periodate solution thereto. After being reacted at room temperature for 2 hours, excessive sodium periodate was removed by gel filtration (PD-10; GE Healthcare), and a streptavidin (SA) solution and a CAPS solution (10%) were added and reacted at room temperature for 5 hours to introduce the streptavidin into dextran. In addition, in order to stabilize a reaction product, 1 mg of Dimethylamine Borate (DMBA; Seikagaku Corporation) and 0.4 mL of 1 M tris solution were added, mixed and reacted at room temperature overnight. Thereafter, the reaction product was purified by gel filtration (Sephacryl S-300HR 1.6×30; GE Healthcare) to obtain a dextran-SA conjugate. Next, the dextran-SA conjugate was prepared using 0.1 M phosphate buffer (pH 7.0) so as to become 2 mg/mL, and 0.5 mL of the dextran-SA conjugate solution was mixed with 5 µL of a maleimide reagent EMCS (DOJINDO LABORATORIES) dissolved in dimethylformamide so as to become 10 mg/mL, and then reacted at room temperature for 1.5 hours. The reaction product was purified by gel filtration with PD-10 (GE Healthcare) to remove unreacted EMCS thereby obtaining the dextran-SA conjugate introduced with one or more maleimide groups. On the other hand, Fab's of c11-9 and c11-14 were produced by the method described in Example 2 and then the Fab's were mixed equally in quantity to prepare 0.5 mg/mL of a Fab'solution. Next, 1 mL of the 0.5 mg/mL Fab'solution was added to 0.5 mL of the 2 mg/mL dextran-SA conjugate introduced with one or more maleimide groups, and reacted at 4° C. overnight. Thereafter, 2-mercaptoethylamine was added thereto so that the final concentration of 2-mercaptoethylamine became 15 mM, and reacted at room temperature for 1 hour thereby blocking unreacted maleimide groups. After being reacted, the solution was purified by gel filtration with Sephacryl S-300HR column (GE Healthcare) to obtain a complex of dextran, SA and Fab'. The amount of the SA contained in the purified complex of dextran, SA and Fab' was determined using, as an indicator, the color development by HABA reagent, as well as SA solution having a known concentration as a standard. The produced polymer of dextran T2000, SA and Fab' was prepared with 0.1 M phosphate buffer so that the SA concentration became 570 nM. 3.0 μL of 61 biotinylated luciferase (Kikkoman Corp.) was added to 300 μL of said polymer solution of dextran T2000, SA and Fab', and reacted at 25° C. for 1 hour to complete the production of a polymerized labeled antibody by applying a previous method.

Enzyme Immunoassay by Using a Luciferase-Labeled Antibody

Anti-HCV core antigen mouse monoclonal antibodies c11-3, c11-7, and AOT3 were immobilized onto magnetic particles by a carbodiimide method using WSC to produce 0.2% antibody-immobilized magnetic particles. On the other hand, each 100 μL of normal human serum and two HCV core antigen positive sera was mixed with 100 μL of a sample treatment solution (6 M guanidine hydrochloride, 0.5 N HCl, 12.5% TritonX100 and 0.75% Tween20) and then reacted at 37° C. for 15 minutes to complete the pretreatment of the sample. After the pretreatment, 140 μL of a reaction solution (0.1 M sodium phosphate, 0.15 M NaCl, 1% BSA, 0.5% casein and 0.05% Tween20, pH 7.3) and 20 μL of 1 M tris buffer were mixed, and then the total 160 μL of this mixed solution was mixed with 80 μL of the pretreated sample thereby neutralizing the sample.

Next, 20 μL of the 0.2% antibody-immobilized magnetic particles were added to 240 μL of the neutralized pretreated sample, and left at 37° C. for 15 minutes to complete a primary reaction. After being reacted, the magnetic particles were washed with a washing solution three times and then thereto were mixed with the luciferase-labeled IgGs produced in Example 5, the complex of luciferase-labeled IgG and dextran (T2000) produced in Example 10 and the polymerized labeled antibody produced by applying a previous method. Each 120 μL of the labeled antibodies which had been diluted so as to set the luciferase concentration to be 18 nM was added, stirred and thereafter reacted at 37° C. for 15 minutes. After being reacted, the magnetic particles were washed with a washing solution three times and resuspended in 100 μL of 50 mM tris buffers (pH 8.5).

100 μL of a substrate solution (luciferin) was added to a tube in which the magnetic particles had been resuspended, followed by measuring the luminescence of luciferase using Lumat LB9507 (Berthold). The luminescence measurement was conducted in such a way that luminescence was integrated for 5 seconds from 0.5 second after adding luciferin. As a result, as shown in Table 3, the complex of luciferase-labeled IgG and dextran (T2000) showed a higher reactivity than the polymerized labeled antibody produced by applying a previous method. When estimated from the S/N ratio of the panel samples L and M, the reactivity of the complex of luciferase-labeled IgG and dextran (T2000) was improved by approximately 3 to 5 times than that of the polymerized labeled antibody produced by applying a previous method. Incidentally, in the case of the polymerized labeled antibody produced by applying a previous method, the S/N ratio was not greatly improved even though the amount of antibody to be used was increased.

TABLE 3

| Labeled antibody | Normal human serum | Positive serum L | Positive serum M | L/Normal | M/Normal |
|---|---|---|---|---|---|
| c11-9 IgG antibody | 218 | 216 | 314 | 1.0 | 1.4 |
| c11-14 IgG antibody | 901 | 869 | 3,453 | 1.0 | 3.8 |
| c11-9 + c11-14 IgG-T2000 | 1,611 | 10,817 | 252,624 | 6.7 | 156.8 |
| Polymerized labeled antibody by applying a previous method | 1,242 | 1,792 | 72,601 | 1.4 | 58.4 |
| | (Luminescence value) | | | (Luminescence ratio) | |

EXAMPLE 16

Application to Biotinylated POD

Production of POD-Labeled Fab'

8.1 μL of 56.8 μM biotinylated POD (Invitrogen Corporation) was added to 30 μL of the 15.4 μM Fab'-streptavidin conjugates (c11-9 and c11-14) produced in Example 6, and reacted at 4° C. overnight to produce POD-labeled Fab's.

Introduction of Biotinylated POD into a Complex of Fab'-Streptavidin Conjugate and Dextran (T2000)

The complex of Fab'-streptavidin conjugate and dextran (T2000), wherein the c11-9 and c11-14 were mixed, produced in Example 11 was prepared with 0.1 M phosphate buffer (pH 7.2) so that the concentration of the Fab'-streptavidin conjugate became 1.4 μM. 1.2 μL of 56.8 μM biotinylated POD (Invitrogen Corporation) was added to 504 of said complex solution, and reacted at 4° C. overnight to produce a complex of POD-labeled Fab' and dextran (T2000).

Enzyme Immunoassay by Using a POD-Labeled Antibody

Anti-HCV core antigen mouse monoclonal antibodies c11-3, c11-7, and AOT3 were immobilized onto magnetic particles by a carbodiimide method using WSC to produce 0.2% antibody-immobilized magnetic particles. On the other hand, recombinant HCV core antigen (c11) was diluted with normal human serum so as to become each 0, 0.12 and 1.2 nM. Each 100 μL of these samples was mixed with 100 μL of a sample treatment solution (6 M guanidine hydrochloride, 0.5 N HCl, 12.5% TritonX100 and 0.75% Tween20) and then reacted at 37° C. for 15 minutes to complete the pretreatment of the sample. Then, 1404 of a reaction solution (0.1 M sodium phosphate, 0.15 M NaCl, 1% BSA, 0.5% casein and 0.05% Tween20, pH 7.3) and 20 μL of 1 M tris buffer were mixed, and then the total 160 μL of this mixed solution was mixed with 80 μL of the pretreated sample thereby neutralizing the sample.

Next, 20 μL of the 0.2% antibody-immobilized magnetic particles were added to 240 μL of the neutralized pretreated sample, and reacted at 37° C. for 15 minutes to complete a primary reaction. After being reacted, the magnetic particles were washed with a washing solution three times and then thereto were mixed with the POD-labeled Fab' and the complex of POD-labeled Fab' and dextran (T2000) produced by the above-mentioned method. Each 120 μL of the labeled antibodies which had been diluted so as to set the POD concentration to be 18 nM was added, stirred and thereafter reacted at 37° C. for 15 minutes. After being reacted, the magnetic particles were washed with a washing solution three times.

200 μL of a substrate solution (luminol) was added to a tube in which the magnetic particles were included, followed by measuring the luminole chemiluminescence catalyzed by POD using Lumat LB9507 (Berthold). The luminescence measurement was conducted in such a way that luminescence was integrated for 3 seconds from 12 seconds after adding luminol. As a result, as shown in Table 4, the complex of POD-labeled Fab' and dextran (T2000) showed a higher luminescence value than the POD-labeled Fab', and the amplification of a signal by the present invention was confirmed similarly to the case of luciferase. The above result showed that the present invention can be performed by using an enzyme other than luciferase.

TABLE 4

| Labeled antibody | Normal human serum (0 nM core antigen) | 0.12 nM core antigen | 1.2 nM core antigen | 0.12 nM/ Normal | 1.2 nM/ Normal |
|---|---|---|---|---|---|
| c11-9 Fab'- POD | 2,757 | 2,251 | 4,627 | 0.8 | 1.7 |
| c11-14 Fab'- POD | 3,049 | 3,450 | 8,850 | 1.1 | 2.9 |
| c11-9 + c11-14 Fab'- T2000 POD | 3,124 | 24,395 | 179,264 | 7.8 | 57.4 |
| | (Luminescence value) | | | (Luminescence ratio) | |

EXAMPLE 17

Application to Biotinylated FITC

Production of FITC-Labeled Fab'

2.9 μL of 160 μM biotinylated FITC (Invitrogen Corporation) was added to 30 μL of the 15.4 μM Fab'-streptavidin conjugates (c11-9 and c11-14) produced in Example 6, and reacted at 4° C. overnight to produce FITC-labeled Fab's.

Introduction of Biotinylated FITC into a Complex of Fab'-Streptavidin Conjugate and Dextran (T2000)

The complex of Fab'-streptavidin conjugate and dextran (T2000), wherein the c11-9 and c11-14 were mixed, produced in Example 11 was prepared with 0.1 M phosphate buffer (pH 7.2) so that the concentration of the Fab'-streptavidin conjugate became 6.3 μM. 20 μL of the complex solution was mixed with 1.0 μL of 160 μM biotinylated FITC (Invitrogen Corporation) and then reacted at 4° C. overnight to produce a complex of FITC-labeled Fab' and dextran (T2000).

Fluorescence Immunoassay by Using a FITC-Labeled Antibody

Anti-HCV core antigen mouse monoclonal antibodies c11-3, ell-7, and AOT3 were immobilized onto magnetic particles by a carbodiimide method using WSC to produce 0.2% antibody-immobilized magnetic particles. On the other hand, recombinant HCV core antigen (c11) was diluted with normal human serum so as to become each 0, 0.12 and 1.2 nM, and then 100 μL of these samples were mixed with 100 μL of a sample treatment solution (6 M guanidine hydrochloride, 0.5 N HCl, 12.5% TritonX100 and 0.75% Tween20) and reacted at 37° C. for 15 minutes to complete the pretreatment of the sample. Then, 140 μL of a reaction solution (0.1 M sodium phosphate, 0.15 M NaCl, 1% BSA, 0.5% casein and 0.05% Tween20, pH 7.3) and 20 μL of 1 M tris buffer were mixed, and the total 160 4 of the mixed solution was mixed with 80 μL of the pretreated sample thereby neutralizing the sample.

Next, 20 μL of the 0.2% antibody-immobilized magnetic particles were added to 240 μL of the neutralized pretreated sample, and reacted at 37° C. for 15 minutes to complete a primary reaction. After being reacted, the magnetic particles were washed with a washing solution three times and then thereto were mixed with the FITC-labeled Fab's and the complex of FITC-labeled Fab' and dextran (T2000) produced by the above-mentioned method. Each 200 μL of the labeled antibodies which had been diluted so as to set the FITC concentration to be 65 nM was added, stirred and thereafter reacted at 4° C. overnight. After being reacted, the magnetic particles were washed in a washing solution three times.

Figure 6:
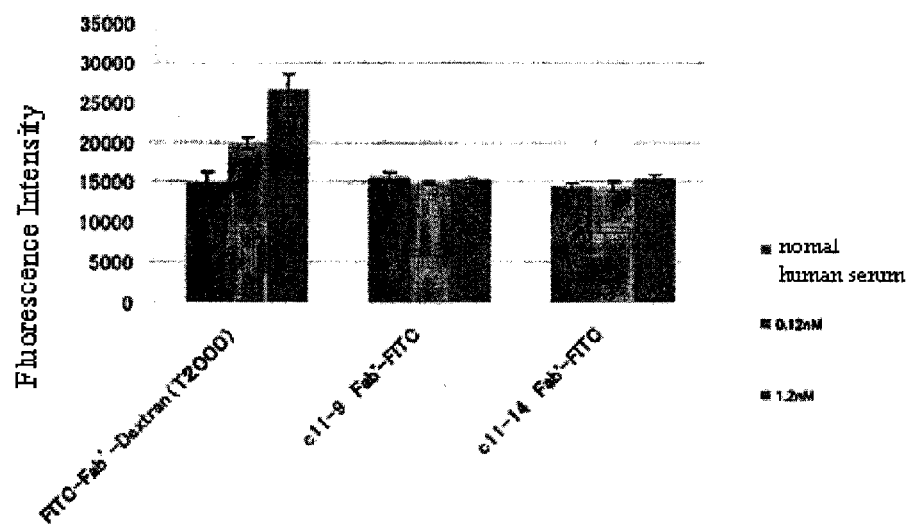
FIG. 6 is a comparison of reactivity between FITC-labeled Fab' and a complex of FITC-labeled Fab' and dextran.

Next, 200 μL of 10 mM PBS (pH 7.4) was added to a tube wherein the magnetic particles were included to suspend the magnetic particles and dispense the suspension into a 96-hole white plate (Thermo Fisher). Thereafter, fluorescence of FITC was measured using a fluorescent plate reader infinite200 (Tecan). The conditions of measuring the fluorescence were such that 485 nm wavelength was used for excitation, while 535 nm fluorescence was detected. As a result, as shown in Table 5 and FIG. 6, the complex of FITC-labeled Fab' and dextran (T2000) showed a higher fluorescent activity than the FITC-labeled Fab's, and the amplification of a signal by the present invention was confirmed similarly to the case of luciferase and POD. The above result showed that the present invention can be performed even by using a low-molecular label which is not an enzyme.

TABLE 5

| Labeled antibody | Normal human serum (0 nM core antigen) | 0.12 nM core antigen | 1.2 nM core antigen | 0.12 nM/ ΔFluorescence intensity | 1.2 nM/ ΔFluorescence intensity |
|---|---|---|---|---|---|
| c11-9 Fab'- FITC | 15,688 | 14,901 | 15,223 | −787 | −465 |
| c11-14 Fab'- FITC | 14,510 | 14,533 | 15,469 | 23 | 959 |
| c11-9 + c11-14 Fab'- T2000- FITC | 15,066 | 19,832 | 26,506 | 4,765 | 11,439 |
| | (Fluorescence intensity) | | | | |

EXAMPLE 18

Accelerated Stability of the Complex of Labeled Probes and a Water-Soluble Carrier The accelerated stability of the complex of labeled probes and a water-soluble carrier according to the present invention was tested. Specifically, with regard to the complex of luciferase labeled c11-9–c11-14 Fab' and dextran (T2000) produced in Example 12, the activity under 4° C. preservation and the remaining activity after an acceleration condition at 37° C. for one week were measured and compared for studies. The activities were measured by the same method as Example 13. The results were as shown in Table 6.

TABLE 6

|  | Normal human serum | Positive serum L | Positive serum M | L/ Normal | M/Normal |
|---|---|---|---|---|---|
| 4° C.-preservation | 260 | 2,573 | 238,771 | 9.9 | 917.2 |
| 37° C. for one week | 257 | 2,346 | 207,284 | 9.1 | 806.6 |
| Remaining activity 4° C./37° C. | 99.8% | 91.1% | 86.9% | 92.2% | 87.8% |

The above results verified that the complex of labeled probes and a water-soluble carrier according to the present invention showed an excellent accelerated stability. That is to say, it was observed that the complex of labeled probes and a water-soluble carrier according to the present invention retained a remaining activity of approximately 90% or more even though preserved at 37° C. for one week. Further, no increase in the background in accordance with the acceleration condition was observed.

These results verified that the present invention allowed to obtain a high-sensitive and stable complex of labeled probes and a water-soluble carrier, which specifically binds to a target substance, and the use of this complex of labeled probes and a water-soluble carrier allowed more sensitive and stable detection and measurement as compared with the prior art. Further, it was verified that the present invention was also effective for a low-molecular label which is not an enzyme.

INDUSTRIAL APPLICABILITY

In a method for detecting and measuring a target substance in a sample by utilizing a specific binding of the target substance and probe, the use of the complex of labeled probes and a water-soluble carrier according to the present invention allows more sensitive and stable detection and measurement as compared with the prior art.

The invention claimed is:

1. A method for producing a complex of labeled probes and a water-soluble carrier, comprising the following steps:
   (a) reacting a probe having one or more thiol groups with an avidin compound having one or more maleimide groups to obtain a probe conjugate, wherein the probe is selected from the group consisting of protein G, protein A, protein L, lectin, and at least one antibody or antigen binding fragment thereof that is selected to bind to a target substance;
   (b) introducing one or more thiol groups into the probe conjugate and reacting said probe conjugate having one or more thiol groups with a high-molecular water-soluble carrier having one or more maleimide groups to obtain a complex of the probe conjugate and the water-soluble carrier;
   (c) mixing the complex of the probe conjugate and the water-soluble carrier with a biotinylated label so that the avidin compound in the complex of the probe conjugate and the water-soluble carrier reacts with biotin in the biotinylated label to form the complex of labeled probes and the water-soluble carrier; and
   (d) isolating the complex of labeled probes and a water-soluble carrier.

2. The method according to claim 1, wherein the avidin compound is avidin or streptavidin.

3. The method according to claim 1, wherein the water-soluble carrier has a molecular weight of 500,000 or more.

4. The method according to claim 1, wherein the water-soluble carrier is selected from the group consisting of dextran, aminodextran, dextrin, cluster dextrin, ficoll, and pullulan.

5. The method according to claim 1, wherein the probe being capable of binding to a target substance is the at least one antibody or antigen binding fragment thereof.

6. The method according to claim 1, wherein the probe being capable of binding to a target substance is two or more kinds of antibodies or antigen binding fragments thereof.

7. The method according to claim 5, wherein the antibody or the antigen binding fragment thereof is selected from the group consisting of Fab', F(ab')$_2$, Fab, IgG, and a combination thereof.

8. The method according to claim 1, wherein the biotinylated label is selected from the group consisting of biotinylated luciferase, biotinylated alkaline phosphatase, biotinylated peroxidase (POD), biotinylated glucose oxidase (GOD), biotinylated fluorescein isothiocyanate (FITC), biotinylated acridinium, biotinylated acridinium derivative, and biotinylated tris(2,2'bipyridyl)ruthenium(II).

9. The method according to claim 8, wherein the biotinylated luciferase is produced by genetic recombination.

10. A complex of labeled probes and a water-soluble carrier produced by a method comprising the following steps:
   (a) reacting a probe having one or more thiol groups with an avidin compound having one or more maleimide groups to obtain a probe conjugate, wherein the probe is selected from the group consisting of protein G, protein A, protein L, lectin, and at least one antibody or antigen binding fragment thereof that is selected to bind to a target substance;
   (b) introducing one or more thiol groups into the probe conjugate and reacting said probe conjugate having one or more thiol groups with a high-molecular water-soluble carrier having one or more maleimide groups to obtain a complex of the probe conjugate and the water-soluble carrier;
   (c) mixing the complex of the probe conjugate and the water-soluble carrier with a biotinylated label so that the avidin compound in the complex of the probe conjugate and the water-soluble carrier reacts with biotin in the biotinylated label to form the complex of labeled probes and the water-soluble carrier; and
   (d) isolating the complex of labeled probes and a water-soluble carrier.

11. The complex of labeled probes and a water-soluble carrier of claim 10, wherein the avidin compound is avidin or streptavidin.

12. The complex of labeled probes and a water-soluble carrier of claim 10, wherein the water-soluble carrier has a molecular weight of 500,000 or more.

13. The complex of labeled probes and a water-soluble carrier of claim 10, wherein the water-soluble carrier is selected from the group consisting of dextran, aminodextran, dextrin, cluster dextrin, ficoll, and pullulan.

14. The complex of labeled probes and a water-soluble carrier of claim 10, wherein the probe being capable of binding to a target substance is the at least one antibody or antigen binding fragment thereof.

15. The complex of labeled probes and a water-soluble carrier of claim 10, wherein the probe being capable of binding to a target substance is two or more kinds of antibodies or antigen binding fragments thereof.

16. The complex of labeled probes and a water-soluble carrier of claim 14, wherein the antibody or antigen binding fragment thereof is selected from the group consisting of Fab', $F(ab')_2$, Fab, IgG, and a combination thereof.

17. The complex of labeled probes and a water-soluble carrier of claim 10, wherein the biotinylated label is selected from the group consisting of biotinylated luciferase, biotinylated alkaline phosphatase, biotinylated peroxidase (POD), biotinylated glucose oxidase (GOD), biotinylated fluorescein isothiocyanate (FITC), biotinylated acridinium, biotinylated acridinium derivative, and biotinylated tris(2,2'bipyridyl)ruthenium(II).

18. The complex of labeled probes and a water-soluble carrier of claim 17, wherein the biotinylated luciferase is produced by genetic recombination.

19. The method according to claim 6, wherein the antibodies or the antibody fragments are selected from the group consisting of Fab', $F(ab')_2$, Fab, IgG, and a combination thereof.

* * * * *